US009132157B2

(12) United States Patent
Kodo et al.

(10) Patent No.: US 9,132,157 B2
(45) Date of Patent: Sep. 15, 2015

(54) ORAL DOSAGE COMPOSITION

(71) Applicant: SPIRULINA BIO-LAB CO., LTD., Osaka-shi, Osaka (JP)

(72) Inventors: Yasumasa Kodo, Osaka (JP); Hiroshi Nishigaki, Kobe (JP)

(73) Assignee: SPIRULINA BIO-LAB CO., LTD., Osaka (JP)

( * ) Notice: Subject to any disclaimer, the term of this patent is extended or adjusted under 35 U.S.C. 154(b) by 0 days.

(21) Appl. No.: 13/846,768

(22) Filed: Mar. 18, 2013

(65) Prior Publication Data

US 2013/0236421 A1 Sep. 12, 2013

Related U.S. Application Data

(62) Division of application No. 12/937,725, filed as application No. PCT/JP2009/050034 on Jan. 6, 2009, now abandoned.

(30) Foreign Application Priority Data

Apr. 15, 2008 (JP) ................................. 2008-105753

(51) Int. Cl.
  *A61K 35/74* (2015.01)
  *A61K 35/748* (2015.01)
  *A23L 1/30* (2006.01)

(52) U.S. Cl.
  CPC ............. *A61K 35/748* (2013.01); *A23L 1/3002* (2013.01); *A61K 35/74* (2013.01)

(58) Field of Classification Search
  None
  See application file for complete search history.

(56) References Cited

U.S. PATENT DOCUMENTS

| 7,326,558 B2 * | 2/2008 | Sakakibara et al. | ....... 435/257.1 |
| 2006/0210545 A1 * | 9/2006 | Sakakibara et al. | ....... 424/93.45 |

FOREIGN PATENT DOCUMENTS

| CN | 1833661 A | 9/2006 |
| JP | 7-289201 A | 11/1995 |
| JP | 2001-190244 A | 7/2001 |
| JP | 2004-238519 A | 8/2004 |
| JP | 2004-256478 A | 9/2004 |
| JP | 2006-230272 A | 9/2006 |
| JP | 2007-215507 A | 8/2007 |

OTHER PUBLICATIONS

Falquet (1996) "The Nutritional Aspects of Spirulina", Published online by Antenna Technologies, London, UK., pp. 1-25 (http://antenna.ch/en/documents/AspectNut_UK.pdf).*
http://www.australianspirulina.com.au/spirulina/spirulina.html, Published by TAAU Austrailia Pty Ltd., Karama, AU, No author, journal, volume, issue, or pages, published Jan. 24, 2005.*
Google search result retrieved Dec. 1, 2013 at https://www.google.com/search?q=how+is+spirulina+ingested+in+chad%3F&rls=com.microsoft%3Aen-us%3AIE-SearchBox&sa=X&ei=HM6bUr2bCavisAShzYGYAg&ved=0CB4QpwUoBg&source=lnt&tbs=cdr%3A1%Ccd_min%3A1%2F1%2F1900%2Ccd_max%3A1%2F6%2F2008&tbm=, no journal, volume, issue, or pages.*
http://www.australianspirulina.com.au/spirulina/productinfomation.htm, Published by TAAU Austrailia Pty Ltd., Karama, AU, No author, journal, volume, issue, or pages, published Jan. 24, 2005.*
https://www.truestarhealth.com/Notes/2810006.html, published online Feb. 1, 2001 by Truestar Health, Toronto, Ontario, Canada, no Author, no. Journal, no Volume, no pages, 4 pages long.*
International Search Report for the Application No. PCT/JP2009/050034 mailed Apr. 14, 2009.
Opinion of the International Preliminary Examining Authority (PCT/IPEA/408) dated May 18, 2010.
International Preliminary Examination Report (PCT/IPEA/409) dated Aug. 10, 2010.
The First Office Action for the Application No. 200980113164.2 from The State Intellectual Property Office of the People's Republic of China dated Sep. 26, 2011.
Rodrígues-Hernández, A. et al., "Spirulina maxima Prevents Fatty Liver Formation in CD-1 Male and Female Mice with Experimental Diabetes", Life Sciences, 2001, vol. 69, pp. 1029-1037.
González De Rivera, C. et al., "Preventative Effect of *Spirulina maxima* on the Fatty Liver Induced by a Fructose-Rich Diet in the Rat, a Preliminary Report", Life Sciences, 1993, vol. 53, No. 1, pp. 57-61.
Torres-Durán, P.V. et al., "*Spirulina maxima* Prevents induction of Fatty Liver by Carbon Tetrachloride in the Rat", Biochemistry and Molecular Biology International, Apr. 1998, vol. 44, No. 4, pp. 787-793.
Ding, Jingling et al., "Effect of Spirulina on Antioxidation Ability of Liver during $CCl_4$ Induced Chronic Liver Injury in Mice", Journal of Lake Sciences, Dec. 2004, vol. 16, No. 4, pp. 343-348.
Estrada, J.E. et al., "Antioxidant Activity of Different Fractions of *Spirulina platensis* Protean Extract", II Farmaco, 2001, vol. 56, pp. 497-500.
Bhat, Vadiraja et al., "Scavenging of Peroxynitrite by Phycocyanin and Phycocyanobilin from *Spirulina platensis*: Protection Against Oxidative Damage to DNA", Biochemical and Biophysical Research Communications, 2001, vol. 285, No. 2, pp. 262-266.
Iwata, Kazuko et al., "Effects of *Spirulina platensis* on Fructose-Induced Hyperlipidemia in Rats", Publication of Japanese Society of Nutrition and Food Science, 1987, vol. 40, No. 6, pp. 463-467.
Iwata, Kazuko et al., "Effects of *Spirulina platensis* on Blood Pressure in Rats", Kagawa Education institute of Nutrition Abstract, 1990, vol. 21, pp. 63-70.
Hayashi, Osamu et al., "Class Specific Influence of Dietary *Spirulina platensis* on Antibody Production in Mice", Journal of Nutritional Science and Vitaminology, 1998, vol. 44, No. 6, pp. 841-851.
Takayama, Fusako et al., "Construction of Non-Alcoholic Steatohepatitis Model Induced by Fatty Liver and Nitrite Administration", Journal of Pharmacological Sciences, 2006, vol. 100, p. 164P.

(Continued)

Primary Examiner — Robert M Kelly
(74) Attorney, Agent, or Firm — Cheng Law Group, PLLC

(57) ABSTRACT

The present invention is an oral dosage composition for prevention and treatment of hepatic inflammation such as NASH. The present invention is an oral dosage composition for prevention or treatment of hepatic inflammation, contains the radical scavenging active spirulina powder effective in preventing, ameliorating, and curing NASH or the like.

4 Claims, No Drawings

(56) References Cited

OTHER PUBLICATIONS

Zhou, Zhan-Ping et al., "Factors That Effect Antioxidant Activity of C-Phycocyanins from *Spirulina platensis*", Journal of Food Biochemistry, 2005, vol. 29, pp. 313-322.

Bhat, Vadiraja et al., "C-Phycocyanin: A Potent Peroxyl Radical Scavenger in Vivo and in Vitro", Biochemical and Biophysical Research Communications, 2000, vol. 275, No. 1, pp. 20-25.

Selmi, Carlo et al., "Non-Alcoholic Fatty Liver Disease: The New Epidemic and the Need for Novel Nutritional Approaches", Journal of Medicinal Food, 2007, vol. 10, No. 4, pp. 563-565.

Kato, Toshimitsu et al., "Effects of Spirulina (*Spirulina platensis*) on Dietary Hypercholesterolemia in Rats", Journal of Japanese Society of Nutrition and Food Sciences, 1984, vol. 73, No. 4, pp. 323-332.

Liu, Qingqing et al., "Clinical Effect Observation of Spirulina in Treatment of Fatty Livers", Journal of Dali University, Aug. 2007, vol. 6, No. 8, pp. 17, 18, and 27.

\* cited by examiner

ORAL DOSAGE COMPOSITION

CROSS REFERENCE TO RELATED APPLICATIONS

This application is a Divisional Application of patent application Ser. No. 12/937,725, filed on Dec. 1, 2010 and abandoned on Jul. 9, 2013, which is a 371 application of Application No. PCT/JP2009/050034, filed Jan. 6, 2009 which is based on Japanese Patent Application No. JP2008-105753 filed on Apr. 15, 2008, the entire contents of which are hereby incorporated by reference.

TECHNICAL FIELD

The present invention relates to oral dosage compositions for at least one of prevention and treatment of hepatic inflammations such as nonalcoholic steatohepatitis (which is referred to as "NASH").

BACKGROUND ART

Fatty liver can be accompanied by hepatic inflammation to cause liver cirrhosis. Even non-alcohol drinkers can suffer from a symptom analogous to an alcoholic steatohepatitis. The symptom is referred to as a nonalcoholic steatohepatitis (NASH), and has attracted attention as a new life-style related disease as well as high blood pressure, diabetes, hyperlipemia.

With increase in the numbers of obese people and patients suffering from life-style related diseases due to the shift to western-style diets such as lipid-rich diets, and lack of physical activity, the numbers of fatty liver patient and NASH patient presumably increase. Hence, it is necessary to develop new medicines for NASH treatment, suppressants for suppressing NASH development, and/or functional foods for reducing risk of NASH occurrence and NASH development, and establish methods of curing NASH and preventing NASH development.

Human NASH is diagnosed by identification of biochemical and histopathological characters of human blood. NASH pathological animal model can be prepared from rats with a partial pressure of oxygen in rat blood being kept at a low level, for evaluation of unknown functional materials.

Non-patent reference 1 (Takayama F. et al: J. Pharmacological Sci., 100 (1), pp.164 (2006).) describes in detail a relationship between the NASH pathological animal model and an oxidative stress. In this reference, the NASH pathological rat model promotes hydroxide radical production at its liver mitochondria, suggesting that it is possible to prevent, alleviate, and cure NASH by promoting hydroxyl radical scavenging activity at its liver mitochondria.

Generally, active oxygen species (ROS) is widely known as an origin of diseases, for example life-style related diseases such as cancer, cataract, nerve disease, kidney disease, allergy, and diabetes. In general, the ROS involving diseases are effectively suppressed by antioxidants.

Non-patent reference 1 shows an experiment using NASH pathological rat model prepared similarly to NASH pathological human model in which liver mitochondria promotes active oxygen radical production, strongly suggesting a relationship between oxidative stress and NASH.

As containing phycocyanin as an effective ingredient, the dried spirulina (e.g., Spirulina platensis) powder has been consumed as a supplement, and can be widely utilized as ingredients of cosmetic and medical products or the like, as described in patent reference 1 (Japanese unexamined patent application publication No. 2007-215507), patent reference 2 (Japanese unexamined patent application publication No. 2004-238519) and patent reference 3 (Japanese unexamined patent application publication No. 2004-256478).

The health functionality of dried spirulina can be attributed to its activities for scavenging ROS, especially lipid-peroxidate (see non-patent reference 2; Vadiraja B. Bhat and K. M. Madyastha: Biochem. Biophys. Res. Commum., 275, pp. 20-25 (2000).), hydroxyl radical (see non-patent reference 3; Pinero Estrada et al: Il Farmaco., 56, pp. 497-500 (2001).), peroxynitrite (see non-patent reference 4; Vadiraja B. Bhat and K. M. Madyastha: Biochem. Biophys. Res. Commum., 285, pp.262-266 (2001).), and so on.

The dried spirulina product is known as an ingredient effective in preventing and curing various diseases. For example, the dried spirulina product can bring various effects such as blood cholesterol suppression effect (non-patent reference 5; Toshimitsu Kato et al., Publication of Japanese Society of Nutrition and Food Science 37(4), 323-332 (1984).), hyperlipidemia alleviation effect (non-patent reference 6; Kazuko Iwata et al., Publication of Japanese Society of Nutrition and Food Science 40 (6), 463-467 (1987).), blood pressure regulation effect (non-patent reference 7; Kazuko Iwata et al., Kagawa Education Institute of Nutrition abstract, 21, 63-70 (1990).). The dried spirulina product can have a UV absorption effect for being applied to skin care medicine (see patent reference 2), as well as immune system enhancement effect and allergic inflammation suppression effect (see non-patent reference 8; Hayashi O. at al., J. Nutr. Sci. Vitaminol., 44, 841-851 (1998) and patent reference 3).

The application of the dried spirulina products to foods and pigments have been proposed as described below, and partially achieved for practical use. The dried spirulina product can be applied to foods (see patent reference 1 and patent reference 4 (Japanese unexamined patent application publication No. 1995-289201). Phycocyanin extracted from the dried spirulina product can be available as a food pigment, as proposed in patent reference 5 (Japanese unexamined patent application publication No. 2001-190244) and patent reference 6 (Japanese unexamined patent application publication No. 2006-230272).

Although the dried spirulina product has a high health functionality, radical scavenging active level of the dried spirulina product for utilizing the functionality has not been determined yet. Besides, the application of dried spirulina product has not been established yet, as to specific use of fermentation products for treatment of life-style related diseases involving active oxygen species.

In view of this circumstance, it is necessary to meet increasing demand for establishment of methods for applying the highly radical-scavenging active dried spirulina products to treatment of life style-related diseases, especially hepatic inflammation such as NASH.

DISCLOSURE OF THE INVENTION

The present invention has been accomplished in view of the above problems, and is intended to provide an oral dosage composition for prevention and treatment of hepatic inflammation such as NASH.

Inventors of the present invention have intensively studied to solve the above problems, and accomplished the present invention for achieving (1) establishment of a highly radical-scavenging active dried spirulina product and techniques for preparation of the same, (2) development of a spirulina-containing synthetic food containing the dried spirulina product, and (3) elucidation of a relationship between NASH and the radical scavenging-activity of the dried spirulina product.

First, the oral dosage composition recited in claim 1 of the present invention is characterized in that it is utilized for at least one of prevention and treatment of hepatic inflammation, and comprises spirulina as an effective ingredient.

Secondly, the oral dosage composition recited in claim 2 of the present invention is characterized in that the hepatic inflammation is NASH.

Thirdly, the oral dosage composition recited in claim 3 as set forth in claim 1 or 2 of the present invention is characterized in that it comprises 0.1% or more by weight of dried spirulina powder.

Fourthly, the oral dosage composition recited in claim 4 as set forth in any one of claims 1 to 3 of the present invention is characterized in that it has a hydroxyl radical scavenging activity with $IC_{50}$ value ranging from 3000 μg/ml to 100 μg/ml determined by an electron spin resonance spectroscopy—spin-trapping method.

The oral dosage composition recited in claim 1 of the present invention enables it to prevent, alleviate and cure the hepatic inflammation mainly due to the radical scavenging activity of spirulina powder, when orally ingested by patients.

The oral dosage composition recited in claim 2 of the present invention enables it to prevent, alleviate and cure NASH mainly due to the radical scavenging activity of spirulina powder, when orally ingested by patients.

The oral dosage composition recited in claim 3 of the present invention enables it to facilitate the prevention, alleviation and treatment of the hepatic inflammation such as NASH.

The oral dosage composition recited in claim 4 of the present invention enables it to facilitate the prevention, alleviation, and treatment of the hepatic inflammation such as NASH mainly due to the radical-scavenging activity of spirulina powder.

BEST MODE FOR CARRYING OUT THE INVENTION

Explanations are given below as to best mode for carrying out the invention.

Spirulina in the present invention is exemplified by Spirulina corakiana, Spirulina crispum, Spirulina labyrinthiformis, Spirulina laxa, Spirulina laxissima, Spirulina major, Spirulina maxima, Spirulina meneghiniana, Spirulina nordstedtii, Spirulina platensis, Spirulina princeps, Spirulina subsalsa, Spirulina subtilissima, Spirulina tenerrima, Spirulina weissii, Spirulina fusiformis, Spirulina jenneri, and the like. In preparation of dried spirulina powder, for example, incubated pure seeds of the above-listed spirulina are cleanly incubated in a pool filled with alkali aqueous solution having a pH of 8 to 11 in a predetermined period, in order to grow spirulina algae. The obtained spirulina algae is isolated, condensed, cleaned, filtered, and dried to provide the dried spirulina powder. The dried Spirulina powder is provided as a food meeting hygiene requirements, as well as having radical scavenging activity.

In this oral dosage composition of the present invention, the dried spirulina can be utilized without further modification. The dried spirulina can be processed into particles, microparticles, or tablets for being easily ingested. The dried spirulina may be mixed with coloring agents, flavors, seasoning agents, or other food additives.

The oral dosage composition in the present invention can be ingested as other foods. The present invention is not limited by particular maximums and minimums of dosage amount, dosage method and dosage period, and other requirements. The oral dosage composition in the present invention can be taken in various ways such as short-time large-dose or long-time small-dose, and or doses combined with other health functional material. But, the present invention is not limited by the above ways. For example, the recommended human dose of this composition may be set in a range of 2 to 10 grams per day.

The oral dosage composition in the present invention can be prepared from the dried spirulina powder alone, or a mixture of the dried spirulina powder and other ingredients such as conventional foods. When added into foods, the dried spirulina powder has a content of 0.1% or more, preferably 1.0% or more, further preferably 5.0% or more by weight with respect to the foods, for providing the oral dosage composition of the present invention as a preferable food effective in preventing and alleviating NASH. But, the maximum content of spirulina in food is not particularly limited in the present invention. The oral dosage composition in the present invention need not be combined with other materials, but may be solely utilized to provide a food with 100% oral dosage composition content. The food for mixed with this oral dosage composition may be powder-like, liquid-like, paste-like, or the like. The content of this oral dosage composition in the food and the way to ingest this oral dosage composition are not particularly limited in the present invention, and can be suitably determined depending on cost and quality requirements such as functionality, and requirements for prevention and treatment of NASH (e.g., species and extent of pathology, dose initiating-time and prescribing time period for ingesting, combined materials, and others).

The oral dosage composition in the present invention can be employed as a composition with its hydroxyl radical-scavenging activity for prevention, alleviation and treatment of NASH pathology. The radical-scavenging activity can be determined in terms of an $IC_{50}$ value by an electron spin resonance—spin trapping method. When having the $IC_{50}$ value in a range of 3000 μg/ml to 100 μg/ml, the oral dosage composition enables to effectively achieve objects of the present invention. When having $IC_{50}$ value less than 100 μg/ml, this composition can not sufficiently provide the objects of the present invention. When having $IC_{50}$ value more than 3000 μg/ml, this composition may bring biological adverse effects due to its excessive radical-scavenging activity. It is noted that each of the above concentrations is the final concentration in an ESR sample solution. The hydroxyl radical-scavenging activity of this oral dosage composition is evaluated relative to that of Trolox. The above hydroxyl radical-scavenging activity corresponds to $IC_{50}$ value in a range of 0.14 to 4.14 μmol (Trolox equivalent/mg) with respect to that of Trorox. The oral dosage composition of the present invention preferably has the radical-scavenging activity with $IC_{50}$ value less than that of Trolox determined by ESR measurement, for being safely utilized as a radical-scavenging active composition for prevention, alleviation and treatment of NASH pathology. The oral dosage composition with hydroxyl-scavenging activity more potent than Trolox may bring unpredictable biological adverse effects, when excessively consumed.

The hydroxyl-scavenging activity of the oral dosage composition in the present invention can be evaluated by means of electron spin resonance—spin trapping method as follows. X-band ESR apparatus (RX-type available from JEOL Ltd.) is employed as a radical detection apparatus, and equipped with a digital high-speed sweeping unit (available from Radical Research Inc.) and an WIN-RAD system RDA-03W ESR data analyzer (available from Radical Research Inc.).

5,5-dimethyl-1-pyrroline-N-oxide (DM PO, available from LABOTEC Co., Ltd.) or 2-(5,5-Dimethyl-2-oxo-2-λ5-[1,3,2]dioxaphosphinan-2-yl)-2-methyl-3,4-dihydro-2 H-pyrrole 1-oxide (CYPMPO available from Radical Research Inc.) is employed as a spin trapping agent. The ESR spectrum were recorded with the following spectrometer parameter settings: sweep range of magnetic field, 336.5±5 mT for DMPO-containing solution or 331.5±10 mT for CYPMPO-containing solution; field modulation, 0.079; time constant, 0.10 sec; sweep time, one minute for DMPO-containing solution or four minutes for CYPMPO-containing solution; output power, 8.0 mW. The evaluation is performed in terms of a relative intensity of the ESR spectrum of DMPO or CYPMPO spin adduct trapping radicals.

In the present invention, the hydroxyl radical-scavenging activity of the sample (the oral dosage composition) is determined in terms of $IC_{50}$ value (μg/ml, final concentration) representing a concentration of the oral dosage composition causing 50% reduction in ESR spectral intensity compared to that of a control solution without containing this composition. Besides, the hydroxyl radical-scavenging activity of Trolox ((±)-Hydroxy-2,5,7,8-tetramethylchromane-2-carboxylic acid available from Aldrich Inc.) is also determined in terms of $IC_{50}$ value (μg/ml, final concentration) representing a concentration of Trolox causing 50% reduction in ESR spectral intensity compared to that of a control solution without containing Trolox. Then, the hydroxyl radical-scavenging activity of the oral dosage composition is determined in terms of $IC_{50}$ value with respect to that of Trolox having the same activity. Namely, Trolox is utilized a reference material, for evaluation of hydroxyl radical-scavenging activity of the sample (the oral dosage composition made of dried spirulina) in terms of a chemical equivalent of Trolox giving the same activity as this sample. In this measurement, it is possible to obtain data with high objectivity and high quantitativity by minimizing errors dependent on ESR apparatus, measurement way, agent purity, and the like.

As described above, the present invention has been achieved to provide the oral dosage composition containing highly radical-scavenging active dried spirulina powder as an effective ingredient for effective prevention, alleviation and treatment of NASH when orally administered to patients.

EXAMPLE

Hereafter, explanations are specifically given as to the present invention with reference to Example. The following Example is intended only to give examples of the present invention. The present invention is not limited to the following Example in any sense.

<Measurement of Hydroxyl Radical Scavenging Activity for the Oral Dosage Composition in the Present Invention (Example 1) and Trolox>

The oral dosage composition in the present invention was prepared as Example 1. The oral dosage composition in Example 1 contains 100% spirulina powder content.

The activity of scavenging free radical and reactive oxygen species was measured by the electron spin resonance (ESR)-spin trapping method for the oral dosage composition in Example 1 prepared in the above way. X-band ESR apparatus (RX-type available from JEOL Ltd.) was employed as a radical detection apparatus, and equipped with a digital high-speed sweeping unit (available from Radical Research Inc.) for measurement with high sensitivity at high speed. Besides, the ESR apparatus was connected to an WIN-RAD system RDA-03W ESR data analyzer (available from Radical Research Inc.). CYPMPO was employed as a spin trapping agent.

The ESR spectrum was recorded with the following spectrometer parameter settings: sweep range of magnetic field, 336.5±5 mT for DMPO-containing solution or 331.5±10 mT for CYPMPO-containing solution; modulation of magnetic field, 0.079 mT; time constant, 0.10 sec; sweep time, one minute for DMPO-containing solution or four minutes for CYPMPO-containing solution; output power, 8.0 mW. The obtained ESR spectrum derives from generation of DMPO spin adduct or CYPMPO spin adduct trapping active oxygen and free radical species in a sample. The concentrations of active oxygen and free radical species in the sample was determined based on signal intensities in the ESR spectrum of the spin adduct. Since a transition metal, Mn gives an ESR spectrum useful as a reference ESR signal, it is possible to precisely determine an ESR signal intensity of DMPO spin adduct (or CYPMPO spin adduct) trapping active oxygen and free radical species, relative to that of Mn, for precise determination of the concentrations of active oxygen and free radical species. The ESR analysis is specifically described below.

In preparation of ESR sample solution, 100 μM ferrous sulfate, 100 μM diethylenetriaminepenta-acetic acid (DETAPAC), 5 mM CYPMPO, the composition of Example 1 or Trolox with various concentrations, and 100 μM hydrogen peroxide were added into 200 mL phosphoric acid buffer (pH: 7.8) which was significantly supplied with nitrogen gas. In preparation of the sample, the above substances except hydrogen peroxide were mixed with each other in advance, and then hydrogen peroxide was supplied to the resultant solution, so as to generate hydroxyl radical through Fenton reaction between hydrogen peroxide and iron ion. ESR measurement was initiated by sweeping magnetic field one-minute after hydrogen peroxide was added, so as to keep constant the reaction time for generating a predetermined amount of hydroxyl radical. The generated hydroxyl radical was trapped by CYPMPO in the ESR sample solution to form the spin adduct (CYPMPO-OH) which gives an eight-line ESR spectrum. The hydroxyl radical concentration in the ESR sample solution was determined in terms of a relative intensity of CYPMPO-OH/Mn ESR signal, by comparison in ESR spectral intensity between a peak in fourth lowest magnetic field in the CYPMPO-OH ESR spectrum and a peak in second lowest magnetic field in six-line Mn ESR spectrum. The relative intensity of CYPMPO-OH/Mn ESR signal for the sample solution containing the composition of Example 1 or Trolox was determined, with respect to that for a control solution not containing the composition of Example 1 or Trolox. The hydroxyl radical-scavenging activity of the oral dosage composition in Example 1 was determined in terms of variation in the relative intensity of CYPMPO-OH/Mn ESR signal obtained for the ESR sample solution containing the composition of Example 1.

The hydroxyl radical-scavenging activity of this composition of Example 1 was determined to be 960 μg/ml in terms of the concentration of this composition of example 1 (the final concentration in the ESR sample solution) causing 50% reduction of the relative intensity of CYPMPO-OH/Mn ESR signal compared to that for the control solution. The determined hydroxyl radical-scavenging activity corresponds to 0.43 μmol Trolox equivalent /mg in terms of the chemical equivalent of Trolox. Accordingly, this composition of Example 1 proved to have a sufficient activity with high health functionality.

<Example of Foods Each Containing the Dried Spirulina Powder of the Oral Dosage Composition in the Present Invention (Examples 2 and 3)>

The dried spirulina powder was mixed with a separate-type dressing, for preparation of the oral dosage composition in Example 2. The dried spirulina powder is a spirulina powder available from Spirulina Bio-Lab Co., Ltd. The separate-type dressing is a commercialized product of Kewpie Corporation. The resultant products contain the dried spirulina powder with different contents of 0.01%, 0.1%, 1.0% and 5.0% by weight based on that of the separate-type dressing.

For preparation of the oral dosage composition in Example 3, the same dried spirulina powder as in the Example 2 was mixed with a noodle commercially available. The resultant products contain the dried spirulina powder with different contents of 0.01%, 0.1%, 1.0% and 5.0% by weight based on that of the noodle.

The products of Examples 2 and 3 were evaluated by ten evaluators. All of the dressings and separate-type dressings containing dried spirulina were judged to be edible by all evaluators, thereby the present invention was confirmed to have a superior quality in respect of functional evaluation.

However, this evaluation revealed that the 0.01 wt % product needs to be consumed in high amount for giving sufficient effectiveness against NASH, thereby showing the 0.01 wt % product is not suitable for practical use in respect of functional evaluation. This evaluation revealed that the oral dosage composition needs to contain the dried spirulina with a content of 0.1 wt % or more.

<The Effectiveness of the Oral Dosage Composition of the Present Invention Against NASH>

The oral dosage compositions of the present invention were administered to NASH biological and pathological model rats, which are raised from fatty liver rats each loaded with oxidative stress (OS) under biological hypoxic condition, in order to evaluate the effectiveness of the oral dosage composition of the present invention against NASH. The evaluation was performed in terms of biochemical variation in blood of the rats, ROS-derivative variation of the liver mitochondria, and pathological variation in liver tissue.

NASH pathological model was prepared from 6-week-old Wister male rats each having a weight of 180 g to 200 g, in accordance with Takayama's method (see non-patent reference 1). For preparation of fatty liver rats, a choline-deficient food (CDHF, available from Oriental Yeast Co., Ltd.) was administered to the male rats in free-feeding for four weeks. CDHF was administered to the rats continuously after four weeks, for maintaining pathological model.

The animals were raised in a polypropyrene opaque cage (width 220, length 320, height 135, available from Natsume Seisakusho Co. Ltd) under 40 to 50% humidity at a temperature of 20° C. to 25° C., with a controlled 12/12 hour light-dark cycle (light on AM 8:00, light off PM 8:00).

For preparation of NASH pathological model rats each loaded with oxidative stress (OS) under biological hypoxic condition, sodium nitrite in physiological salt solution was intraperitoneally administered to the fatty liver rats at 30 mg/kg (body weight) per day for six weeks. During this administration, blood test in tail vein was performed in two-week intervals, for confirmation of normal development of pathological condition.

The oral dosage composition in Example 1 of the present invention was orally administered to the fatty liver rats at 2 g/kg (body weight) per day or 6 g/kg (body weight) per day for six weeks, in free-feeding, instead of the sodium nitrite solution, for evaluation of effectiveness of the oral dosage composition in the present invention against NASH.

After the administration, the rats were sacrificed for observation of biochemical variation in blood thereof, variation in amounts of liver mitochondria-produced active oxygen and free radical species (ROS), and pathological variation in liver tissue.

Explanations are give as to this Example, with reference to group 1 (CDHF+OS), group 2 (CDHF+OS+2 g/kg of Example 1), group 3 (CDHF+OS+6 g/kg of Example 1). Eight rats were used for each group (n=8).

AST and ALT values in plasma was determined with transaminase CII-test Wako (available from Wako Pure Chemical Industries).

The liver mitochondria-produced active oxygen and free radical species (ROS) were detected in the following procedure. The liver was perfused with 1.15% potassium chloride solution (containing 5 mM benzamidine) through inferior vena cava, and then sampled. The sampled liver tissue 1 g was added to a tris hydrochloric acid buffer solution (pH 7.4, containing 0.25 M sucrose and 0.1 M potassium chloride), and then homogenized. Next, the resultant solution was subjected to centrifugal separation at 3000×g for 10 minutes at 4° C. to obtain a supernatant liquid. Subsequently, the obtained supernatant liquid was subjected to centrifugal separation at 9000×g for 20 minutes at 4° C., so as to obtain a precipitation product. The precipitation product was centrifugally washed with tris hydrochloric acid buffer solution (pH 7.4, containing 0.25 M sucrose and 0.1 M potassium chloride) two times, giving mitochondria fractions. Each mitochondria fraction 14.28 mg was diluted with 1 ml of tris hydrochloric acid buffer solution (pH 7.4, containing 0.25 M sucrose and 0.1 M potassium chloride), so as to obtain a sample solution having a concentration of 500 μg/ml in terms of mitochondria protein.

For determination of amounts of produced active oxygen and free radical species (ROS), the obtained liver mitochondria solution 35 μl was mixed with 25 μl of a solution (containing 0.1% dodecyl maltoside, 5 mM glutamate, 5 mM malate, and 200 mM succinate), 20μl of 4.6M DMPO solution and 20 μl of 2 mM NADH solution 20 μl, and then incubated at 37° C. for five minutes. The solution was measured with an ESR apparatus (JESREIX/HR available from JEOL Ltd.), soon after incubated.

Prior to the ESR measurement for the solution, ESR spectral intensity of DMPO spin adduct (DMPO-OH) was determined relative to that of $Mn^{2+}$ in MnO disposed inside the cavity. Namely, ESR spectral intensity of DMPO spin adduct was determined in terms of relative intensity with respect to that of $Mn^{2+}$ (DMPO-OH/Mn).

The ESR spectral data was statistically analyzed by one-dimensional analysis of variance (ANOVA) and subsequent Turkey's multiple-comparison test to be evaluated in terms of "mean value±standard error". The comparison between two groups was analyzed by student's t-test, significance level of 5% or less was determined to be significant.

After the administration, the rats were sacrificed, for observation of biochemical variation in blood of the rats, ROS-productive variation at the liver mitochondria and pathological variation in liver tissue so as to give the following results.

Biochemical measurement tests were performed for group 1 not administered with the dried spirulina product (CDHF+OS), for obtaining the following results regarding variations in biochemical properties before and after administration.

AST value (units/ml) in plasma was found to rise to 140±7 IU/L from 23±2 IU/L.

ALT value (units/ml) in plasma was found to rise to 16±2 IU/L from 7±2 IU/L.

The above results show NASH symptom due to oxidative stress appears.

Biochemical measurement tests were performed for group 2 administered with 2 g/Kg (body weight) (CDHF+OS+2 g/Kg of Example 1), for obtaining the following results regarding variations in biochemical properties before and after administration of 2 g/Kg (body weight) of Example 1.

AST value (units/ml) in plasma was found to rise to 100±20 IU/L from 25±2 IU/L.

ALT value (units/ml) in plasma was found to rise to 14±3 IU/L from 8±2 IU/L.

The above results demonstrate that NASH symptom due to oxidative stress is alleviated by administration of 2 g/Kg (body weight) of the oral dosage composition in Example 1 of the present invention.

Biochemical measurement tests are conducted for group 3 administered with 6 g/Kg (body weight) (CDHF+OS+6 g/Kg of Example 1), for obtaining the following results regarding variations in biochemical properties before and after administration of 6 g/Kg (body weight) of Example 1.

AST value (units/ml) in plasma was found to rise to 35±5 IU/L from 21±3 IU/L.

ALT value (units/ml) in plasma was found to rise to 10±2 IU/L from 7±3 IU/L.

The above results demonstrate that NASH symptom due to oxidative stress is alleviated by administration of 6 g/Kg (body weight) of the oral dosage composition in Example 1 of the present invention.

Hematoxylin-eosin stain was employed to color macrovesicular steatosis in conventional way for confirmation of the pathological variation in liver tissue, giving the following results regarding the accumulation of macrovesicular steatosis.

Group 1 (CDHF+OS) proved to suffer from advanced macrovesicular steatosis and substantial disarray of liver cells.

Group 2 (CDHF+OS+2 g/Kg of Example 1) proved to suffer from moderate macrovesicular steatosis and moderate disarray of liver cells.

Group 3 (CDHF+OS+6 g/Kg of Example 1) proved to suffer from less-advanced macrovesicular steatosis and slight disarray of liver cells.

The above results demonstrate that the macrovesicular steatosis in liver tissue and disarray of liver cells developing with NASH are alleviated by administration of the composition in Example 1, depending on its concentration.

Masson trichrome stain was employed to color collagen fibril in conventional way for confirmation of the pathological variation in liver tissue, giving the following results regarding collagen fibril.

Group 1 (CDHF+OS) proved to suffer from bridging between portal region and central vein region, and pseudolobule formation (F3-F4).

Group 2 (CDHF+OS+2 g/kg of Example 1) proved to suffer from slight bridging between portal region and central vein region.

Group 3 (CDHF+OS+6 g/kg of Example 1) proved to suffer from fibrosis in portal region and in the vicinity of central vein, without bridging.

The above results demonstrate that the bridging and fibrosis developing with NASH are alleviated by administration of the composition in Example 1, depending on its concentration.

Berlin blue stain was employed to detect iron ions in conventional way for confirmation of the pathological variation in liver tissue, giving the following results regarding coloring due to iron precipitation.

Group 1 (CDHF+OS) proved to suffer from substantial iron precipitation between portal region and central vein region.

Group 2(CDHF+OS+2 g/kg of Example 1) proved to suffer from slight iron precipitation between portal region and central vein region.

Group 3 (CDHF+OS+6 g/kg of Example 1) proved to hardly suffer from iron precipitation.

The above results demonstrate that the iron precipitation in liver tissue developing with NASH are alleviated by administration of the composition in the present invention, depending on its concentration.

The above results using NASH model animals confirm the dried spirulina products efficacy for anti-oxidative treatment against NASH, one of typical life style-related diseases.

<Suppression Effects of Liver Mitochondria-Produced Free Radicals With the Use of the Oral Dosage Composition in the Present Invention>

The following tests were performed for confirmation of effectiveness of the oral dosage composition in the present invention, in terms of suppression of active oxygen and free radical generation resulting from energy metabolism in the liver mitochondria of NASH pathological animal model.

The following experiments were performed for rats in groups 1, 2 and 3. NASH pathological model was prepared in accordance with the above Takayama's method (see non-patent reference 1).

Mitochondria fractions were obtained from rats in groups 1, 2 and 3. (See Egashira T. et al: Toxicology Letter, 117, 115-119 (2000)) That is, the liver sample was obtained by perfusing the liver with 1.15% potassium chloride solution (containing 5 mM benzamizine) through an inferior vena cava. The liver tissue 1 g was added to a tris hydrochloric acid buffer solution (pH 7.4, containing 0.25 M sucrose and 0.1 M potassium chloride), and then homogenized. Next, the resultant solution was subjected to centrifugal separation at 3000×g for 10 minutes at 4° C. to obtain a supernatant liquid. Subsequently, the obtained supernatant liquid was subjected to centrifugal separation at 9000×g for 20 minutes at 4° C., so as to obtain a precipitation product. The precipitation product was centrifugally washed with tris hydrochloric acid buffer solution (pH 7.4, containing 0.25 M sucrose and 0.1 M potassium chloride) two times, giving mitochondria fractions.

Subsequently, mitochondria produced-reactive oxygen and free radical species in each group were trapped by a spin-trapping agent, DMPO, to obtain DMPO spin adduct in the following way (see, Yudong Wang et al: Free Radical Biology and Medicine, 36(11), 1434-1443 (2004)). The DMPO spin adduct was detected by ESR spectroscopy. DMPO, mitochondria and NADH were ice-cooled in advance. Other substances were warmed at 37° C. in advance. The assay solution was prepared by adding 35 μl of mitochondria emulsion (containing 0.5 mg of protein), 920 mM of DMPO, 0.1% dodecylmaltoside, 10 mM of potassium L-glutaminate, 10 mM of L(-)-sodium malate, 200 mM of disodium succinate and 100 μM of NADH to a buffer solution (pH 7.4) containing 5 mM of trisaminomethane, 0.25 mM of sucrose and 0.1 mM of potassium chloride. Then, the resultant solution was incubated at 37° C. for 5 minutes, for undergoing ESR measurement.

The mitochondria fraction in each group was suspended with 0.03 M tris-hydrochloric acid buffer solution (pH 7.4, containing 0.25 M sucrose and 0.1 M potassium chloride), and then immediately preserved at −80 ° C. prior to undergoing ESR analysis.

The composition in Example 1 was added to the ESR measurement sample solution for ESR spectroscopic analysis. The composition in Example 1 was examined for evaluation of its efficacy of reducing active oxygen and free radicals (ROS) which are produced due to a disorder of mitochondrial function, in terms of variation in an intensity of ESR spectrum of DMPO spin adduct trapping active oxygen and free radical (see Takayama F. et al: Japanese Journal of Pharmacology, 85, 227-233 (2001)). Specifically, the presence of mitochondria produced-active oxygen and free radicals (ROS) was confirmed by observation of variations in intensities of ESR spectra of DMPO and DMPO-OH trapping active oxygen and free radicals (ROS) with their typical g-values and fine structure parameters. The dried spirulina product was added to the assay solution containing NASH pathological mitochondria. The obtained solution was examined using ESR spectroscopy in terms of variation in relative intensity of ESR spectra (DMPO-OH/Mn), for evaluation of its efficacy of reducing active oxygen and free radical species which are generated due to energy metabolism of NASH-pathological model. The efficacy was evaluated in terms of $IC_{50}$ (µg/ml) representing the concentration of this composition of example 1 causing 50% reduction of the relative ESR signal intensity. The ESR apparatus was operated for ESR measurement in the same way as in "the effectiveness of the oral dosage composition of the present invention against NASH" described above.

The following results were obtained as to the relative signal intensity of ESR spectra arising from the presence of liver mitochondria-produced ROS. The relative signal intensity was determined to be 1.0±0.1 in group 1 (CDHF+OS), 0.8±0.1 in group 2 (CDHF+OS+2 g/Kg of Example 1), and 0.6±0.1 in group 3 (CDHF+OS+6 g/Kg of Example 1), increasing from 0.5±0.1 obtained prior to an addition of oxidative stress. The result shows that the amount of liver mitochondria produced-ROS increasing with NASH development is reduced by administration of the composition in Example 1, depending on its concentration.

The above results demonstrate that the oral dosage composition in the present invention enables to suppress and regulate the radical generation resulting from energy metabolism of liver mitochondria of NASH pathological animal model. Therefore, the oral dosage composition in the present invention proved effective in preventing, alleviating, and curing NASH when orally administered to patients.

The invention claimed is:

1. A method of treating non-alcoholic steatohepatitis comprising:
    administering an oral dosage composition to a patient in need thereof, said oral dosage composition comprising spirulina as an effective ingredient against non-alcoholic steatohepatitis, so as to alleviate bridging, and fibrosis in liver tissue.

2. The method of treating non-alcoholic steatohepatitis as set forth in claim 1, wherein said oral dosage composition comprises 0.1% or more by weight of a dried spirulina.

3. The method of treating non-alcoholic steatohepatitis as set forth in claim 1, wherein said oral dosage composition has a hydroxyl radical scavenging activity with $IC_{50}$) value ranging from 3000 µg/ml to 100 µg/ml determined by electron spin resonance spectroscopy-spin trapping method.

4. The method of treating non-alcoholic steatohepatitis as set forth in claim 1, a dose of said oral dosage composition is set in a range of 2 to 10 grams per day.

* * * * *